(12) United States Patent
Tybinkowski et al.

(10) Patent No.: US 7,174,587 B2
(45) Date of Patent: Feb. 13, 2007

(54) PATIENT POSITIONING DEVICE FOR RADIATION THERAPY

(75) Inventors: Andrew P. Tybinkowski, Boxford, MA (US); Robert F. Riemer, Andover, MA (US); Robert M. Williams, Wilmington, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/966,488

(22) Filed: Oct. 15, 2004

(65) Prior Publication Data

US 2005/0160529 A1 Jul. 28, 2005

Related U.S. Application Data

(60) Provisional application No. 60/512,072, filed on Oct. 17, 2003.

(51) Int. Cl.
*A61G 15/00* (2006.01)
(52) U.S. Cl. .................................. 5/601; 5/622; 5/621
(58) Field of Classification Search ............ 5/621–624, 5/601; 119/755; 128/869–870; 378/208–209
See application file for complete search history.

(56) References Cited

U.S. PATENT DOCUMENTS

| | | | | |
|---|---|---|---|---|
| 5,385,119 | A | * | 1/1995 | Tarulli ........................ 119/755 |
| 5,494,048 | A | * | 2/1996 | Carden ........................... 5/622 |
| 5,537,454 | A | | 7/1996 | Korver, II |
| 5,806,116 | A | | 9/1998 | Oliver et al. |
| 6,161,237 | A | | 12/2000 | Tang et al. |

* cited by examiner

*Primary Examiner*—Patricia Engle
*Assistant Examiner*—Fredrick Conley
(74) *Attorney, Agent, or Firm*—McDermott Will & Emery LLP

(57) ABSTRACT

A patient positioning system for radiation therapy, including an elongated table, a lock bar positioned on the table and extending perpendicular to a length of the table, and first and second clamps secured to opposing ends of the lock bar. The clamps are adapted to grip flat surfaces of sides of the table so as to secure the lock bar in a fixed position along the length of the table. The second clamp is adjustably secured on the lock bar so that the second clamp can be unsecured from the lock bar, the lock bar can be re-positioned on the table as desired, and the second clamp then re-secured to the lock bar to fix the lock bar in place on the table. The system also includes a patient restraint member secured to the lock bar and adapted to extend over a patient lying on the table.

19 Claims, 7 Drawing Sheets

PATIENT POSITIONING DEVICE FOR RADIATION THERAPY

CROSS-REFERENCE TO RELATED APPLICATIONS

The present application claims priority to co-pending provisional U.S. patent application Ser. No. 60/512,072, which was filed on Oct. 17, 2003, is assigned to the assignee of the present application, and is incorporated herein by reference.

FIELD OF THE INVENTION

The present disclosure relates generally to tomography systems and, more particularly, to a table for supporting a sample, such as a patient, in a tomography scanner during a scanning procedure. Even more particularly, the present disclosure is related to a patient positioning device for a patient table.

BACKGROUND OF THE DISCLOSURE

Medical diagnostic imaging and scanning machines such as magnetic resonance imaging (MRI) apparatus, X-ray machines, positron emission tomography (PET) scanners, and computer tomography (CT) scanners are well known. Such machines are quite popular as a tool for diagnosis of tumors and the like. Owing to good quality tomographic images with low dosage X-ray radiation, the CT scanner has become especially well accepted by the medical profession.

An annular gantry normally supports many of the components of a CT scanner and includes an outer ring secured to a stand and an inner ring mounted for rotation within the outer ring. During a scanning procedure, a patient table is positioned through the center of the gantry and the inner ring is rotated about the table. The components supported by the gantry can include an x-ray tube for providing the x-ray beam, one or more high voltage power supplies, balancing weights, a data acquisition module, and a bank of detectors diametrically opposed from the x-ray source. At least some of these components are secured in the inner ring for rotation therewith.

In order to obtain tomographic images of a patient with a CT scanner or X-ray CT apparatus, it is necessary that the patient be located exactly at a predetermined position inside the opening of an annular scan gantry of the apparatus. For this reason, such apparatus has been provided with a patient handling couch or table which is moveable vertically to be in line with an axis of the scan gantry, and moveable axially in and out of the scan gantry. Several patient tables are known for this purpose.

Patient positioning systems are used for accurate and reproducible positioning of a patient for radiation therapy, diagnostic imaging, surgery, and other medical procedures. During these procedures, it is important to immobilize a part or parts of the patient's body. Accurate positioning of the body part is also important in repeat treatments so that the precise same location of the bodies are exposed to the radiation each time. Therefore, different types of devices have been made to immobilize body parts and to index the body to the treatment table to assure proper and repeatable alignment for radiation therapy.

One example of such a patient positioning system is described in U.S. Pat. No. 5,806,116. The positioning system utilizes a tabletop with indentations, or notches, along opposite sides, and a lock bar extending across the tabletop with a disk at each end adapted to be received in opposing indentations. The lock bar is secured to the tabletop with an eccentric cam which tightens the ends of the bar into engagement with the indentations of the tabletop.

Another patient positioning system is described in U.S. Pat. No. 6,161,237, which shows a table having opposite sides with indexing notches along each side. A patient restraint member is registered on an elongated lock bar and is adapted to extend over a portion of the patient's body to position the patient on the table. The lock bar has a downwardly extending circular ball on each end adapted to snap-fit into opposing pairs of the notches on each side of the table.

What is still desired is a new and improved patient positioning system for radiation therapy treatment. Preferably the new and improved system will not rely upon using notches in a patient table, such that the table is easier and less expensive to manufacture and can be repaired if damaged.

SUMMARY OF THE DISCLOSURE

The present disclosure provides a patient positioning system for radiation therapy treatment, including an elongated table having a length extending between opposing ends of the table, and having a width defined between opposing sides of the table, and an elongated lock bar positioned on a top surface of the table and extending perpendicular to the length of the table. The system also includes a first clamp secured at one of two opposing ends of the lock bar, and a second clamp secured at the other of the two opposing ends of the lock bar. The clamps have flat surfaces adapted to grip flat surfaces of the sides of the table so as to lock the lock bar in a fixed position between the opposing ends of the table. Each of the clamps also includes a lip for catching a bottom surface of the table.

The second clamp is adjustably secured on the lock bar so that the second clamp can be unsecured from the lock bar, the lock bar can be re-positioned on the table as desired between the opposing ends of the table, and the second clamp then re-secured to the lock bar to fix the lock bar securely in place on the table. The system also includes a patient restraint member secured to the lock bar and adapted to extend over a portion of a patient lying on the top surface of the table, in order to reproducible position the patient on the table for radiation therapy treatment.

Among other features, advantages and aspects, a patient positioning system constructed in accordance with the present disclosure does not rely upon notches provided in the sides of the patient table. The improved patient positioning system of the present disclosure is particularly useful for accurate and repeatable patient positioning for radiation therapy treatment, as well as for other diagnostic and treatment procedures.

According to one aspect of the present disclosure, the second clamp further includes an adjustment mechanism including a rack secured on the lock bar, a rotatable gear having teeth engaging linear teeth of the rack such that rotation of the gear causes the gear to move linearly with respect to the rack. The rack is oriented on the lock bar such that linear movement of the gear is parallel with a length of the lock bar. An adjustment knob is secured to the gear through a shaft, and extends through a cover of the second clamp.

Additional features, advantages and aspects of the presently disclosed patient positioning system for radiation therapy treatment will become apparent by reference to the following description taken in connection with the accompanying drawings.

BRIEF DESCRIPTION OF THE DRAWINGS

Like reference characters designate identical or corresponding components and units throughout the several views.

DETAILED DESCRIPTION OF AN EXEMPLARY EMBODIMENT OF THE DISCLOSURE

Figure 1:
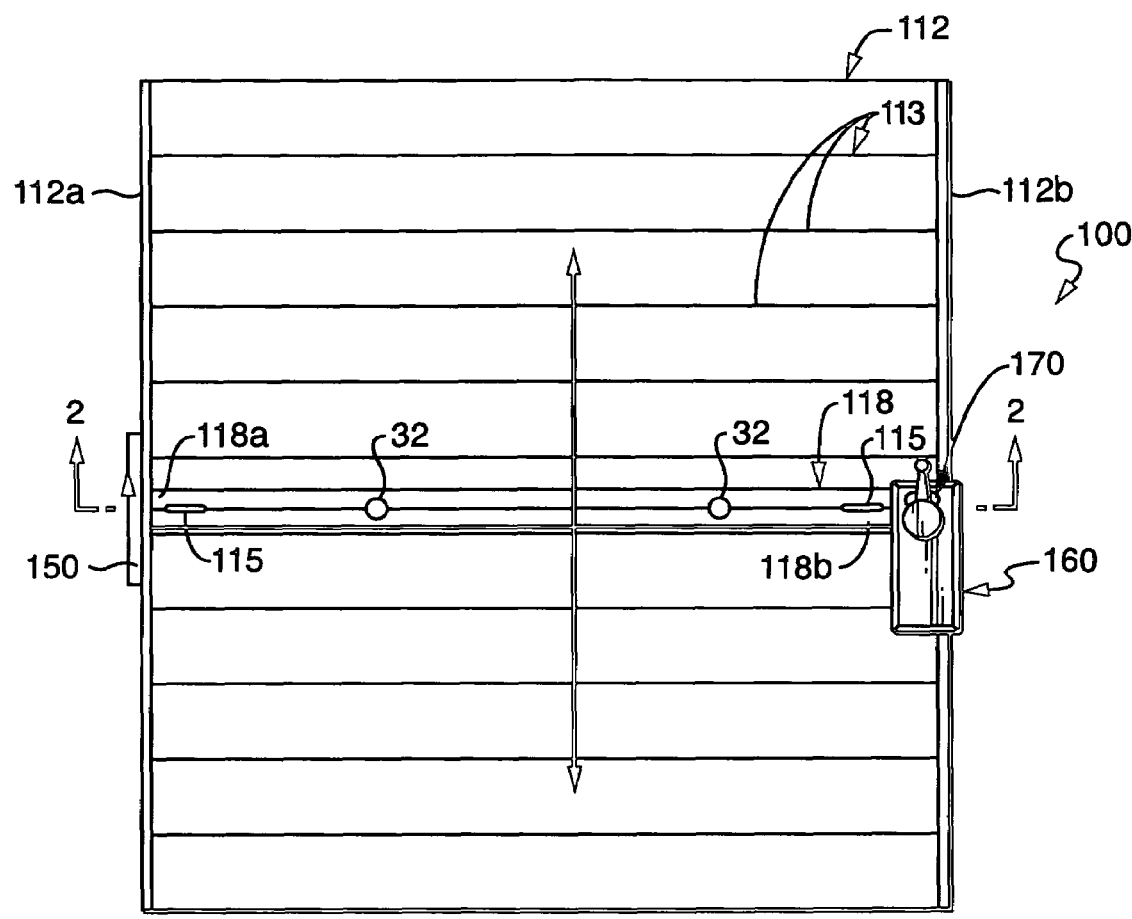
FIG. 1 is a top plan view of an exemplary embodiment of a patient positioning system constructed in accordance with the present disclosure and including a lock bar positioned on a table.
Figure 2:
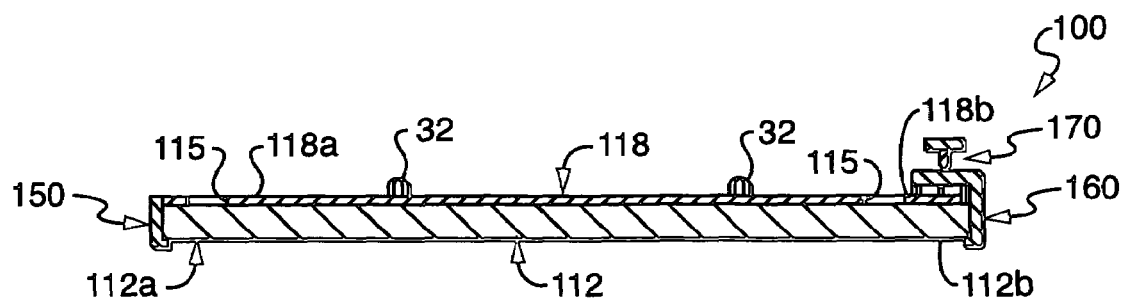
FIG. 2 is a sectional view taken along line 2—2 of FIG. 1 of the lock bar and the table.

Referring to FIGS. 1 through 5, the present disclosure provides a new and improved patient positioning device 100 for radiation therapy treatment. The device 100 includes a table 112 having opposite sides 112*a*, 112*b*. Although not shown, a patient positioning system includes a patient restraint member (such as the patient restraint member shown in FIGS. 6 and 8) registered on an elongated lock bar 118 of the patient positioning device 100 for extending over a portion of a patient's body to repeatably position the patient on the table 112. The lock bar 118 has first and second clamps 150, 160 secured at opposing ends 118*a*, 118*b*, respectively, of the lock bar 118 for engaging the sides 112*a*, 112*b* of the table 112. At least one of the clamps 160 is adjustably secured on the lock bar 118 so that, the clamp 160 can be loosened from the lock bar 118, the lock bar 118 can be re-positioned on the table 112 as desired, and the clamp 160 then re-tightened to fix the lock bar 118 securely in place on the table 112.

The lock bar 118 also includes a pair of upwardly extending studs 32 which are secured to the bar 118 by bolts. The studs 32 are adapted to matingly register with holes of a patient restraint device so that the device is positioned on the lock bar 118.

Among other features, advantages and aspects, a patient positioning device 100 constructed in accordance with the present disclosure does not rely upon notches provided in the sides 112*a*, 112*b* of the table 112. The improved patient positioning device 100 of the present disclosure is particularly useful for accurate and repeatable patient positioning for radiation therapy treatment, as well as for other diagnostic and treatment procedures.

Figure 6:
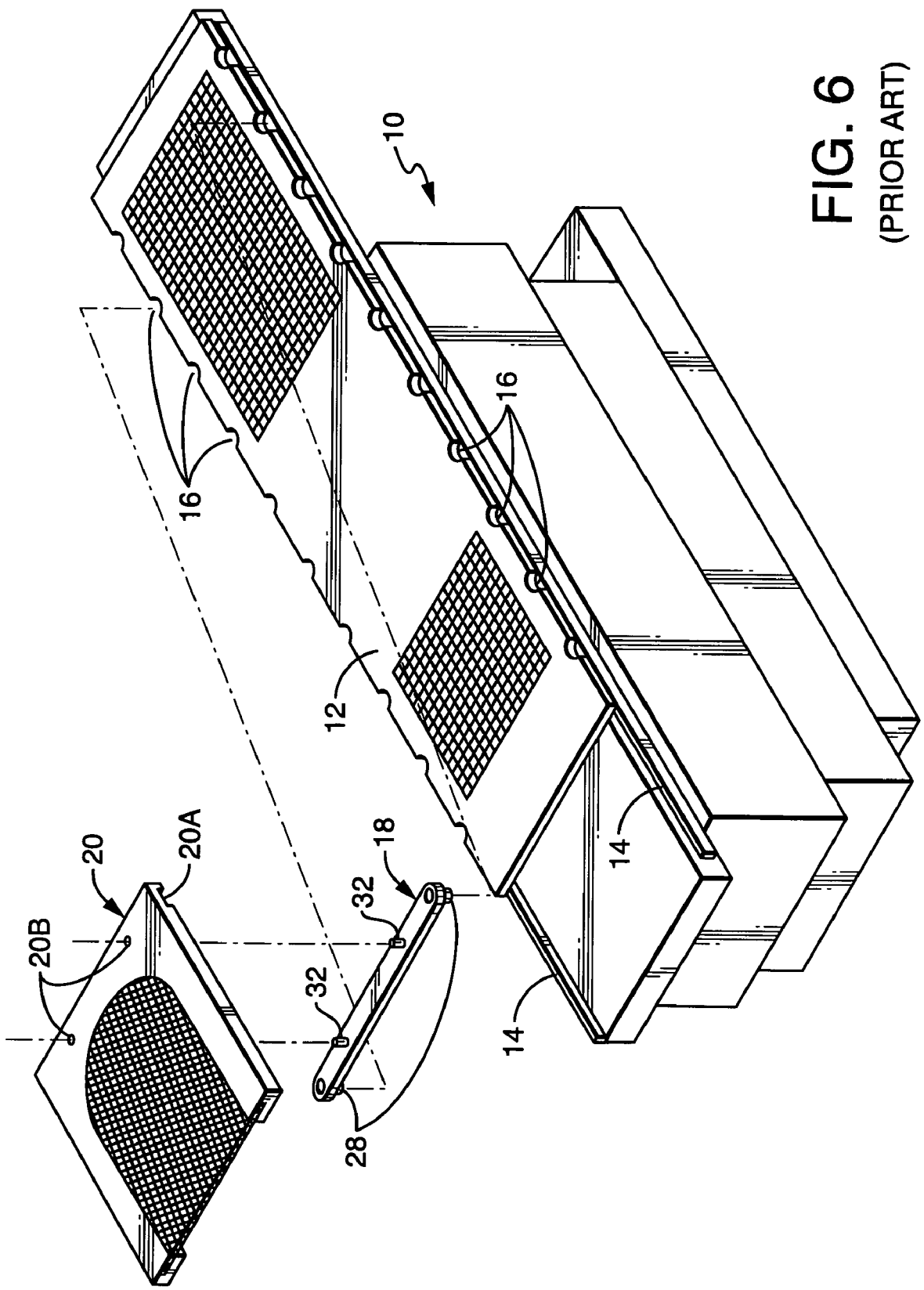
FIG. 6 is an exploded perspective view of a patient positioning system constructed in accordance with the prior art, with a lock bar positioned above a table and a patient fixation device positioned above the lock bar.
Figure 7:
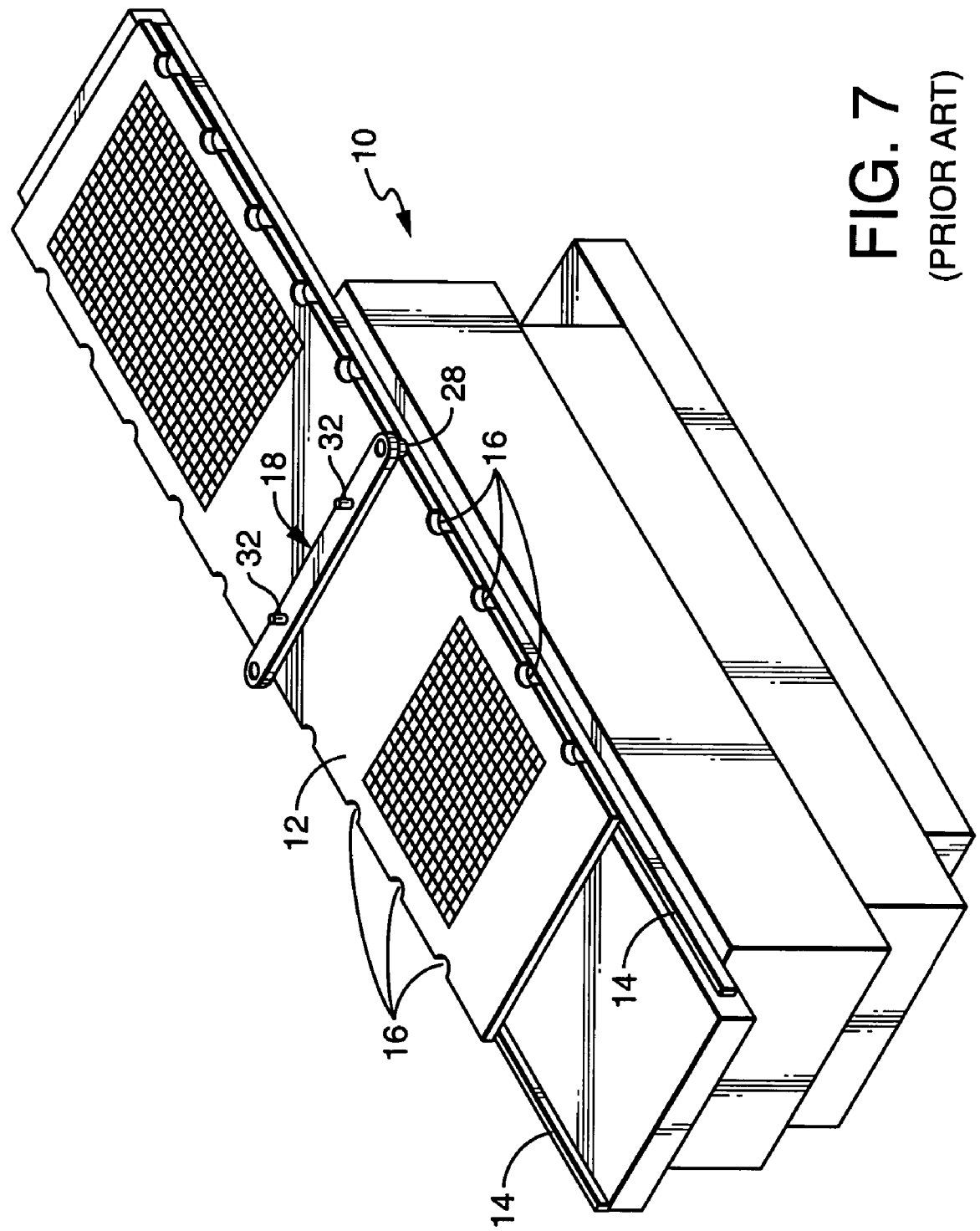
FIG. 7 is a view similar to FIG. 6 showing the lock bar snap-fit into position on the table, with the patient restraint device removed for clarity.
Figure 8:
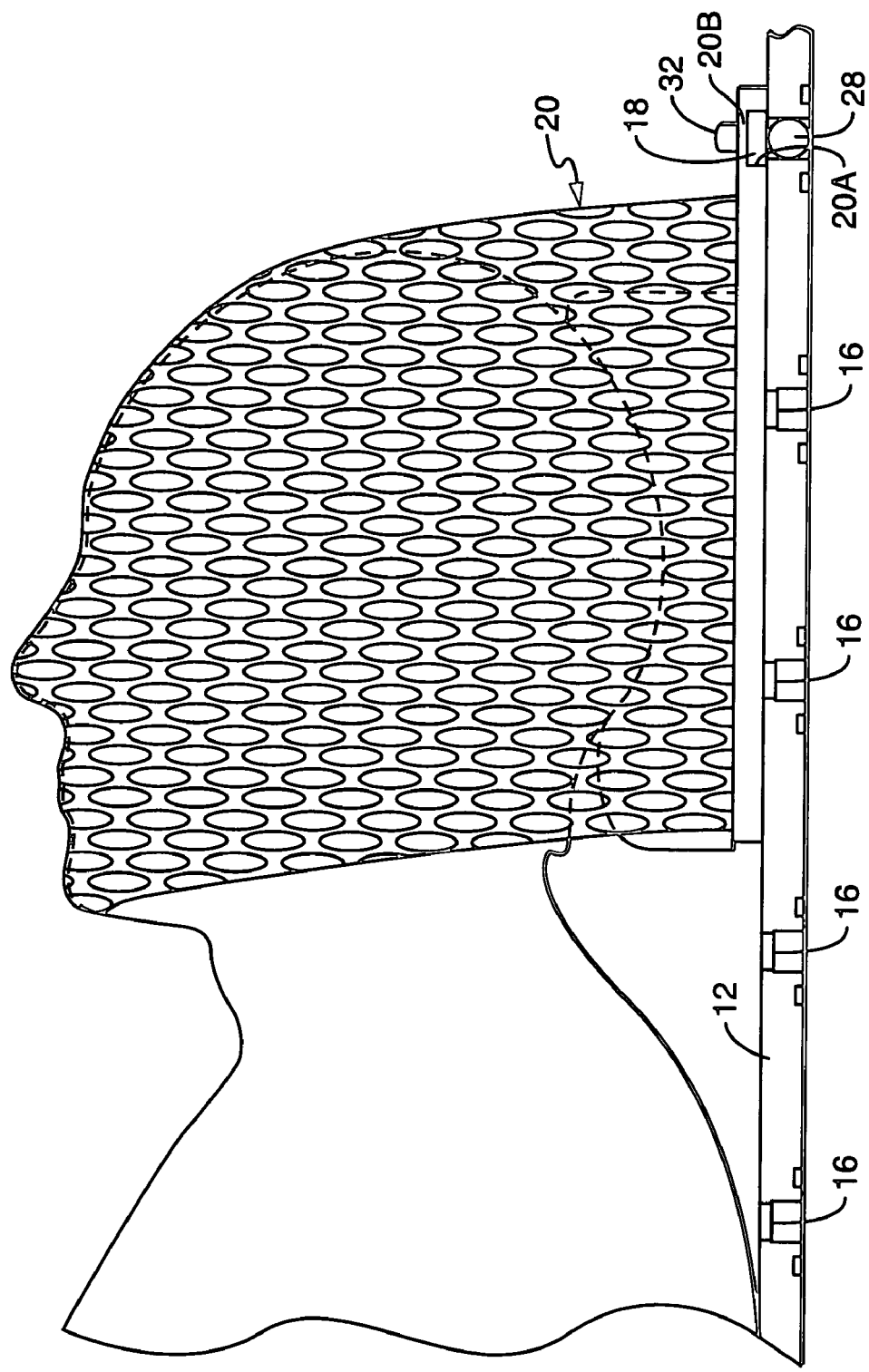
FIG. 8 is a enlarged side elevation view of the patient positioning system of FIG. 6, showing the lock bar snap-fit into position on the table and the patient restraint device attached to the lock bar and securing a patient's head in a fixed position on the table.

Before describing the exemplary embodiment of the new and improved patient positioning device 100 in further detail, however, a patient positioning system constructed in accordance with the prior art will be described to provide useful background information. As seen in FIGS. 6 through 8, a table base or carriage 10 is provided with a table 12. The table 12 is mounted for longitudinal movement upon side rails 14 attached to the opposite sides of carriage 10.

The table 12 has a plurality of notches 16 along opposite sides of the table. The notches 16 are adapted to receive opposite ends of a lock bar 18 to which a patient restraint member 20 is secured. The notches 16 serve as indexes for repeated treatments of individual patients.

The lock bar 18 includes a male extension 28, preferably in the shape of a ball, which is connected to the lock bar 18 with a threaded bolt. The shape of the male extension 28 of the lock bar 18 provides a snap-fit connection between the lock bar 18 and the notches 16 of the tabletop 12. The lock bar 18 also includes a pair of upwardly extending studs 32 which are secured to the bar 18 by bolts. The studs 32 are adapted to matingly register with holes 20B of the patient restraint device 20 so that the device 20 is positioned on the lock bar 18. The device 20 also has a bottom groove 20A sized to receive the bar 18.

In use, the lock bar 18 with the mounted patient restraint 20 is positioned over the patient. The balls 28 of the lock bar 18 are snap-fit into the desired opposing pairs of notches 16 in the tabletop 12 so as to secure the lock bar 18 to the table 12.

Referring again to FIGS. 1 through 5, the patient positioning device 100 constructed in accordance with the present disclosure does not rely upon notches provided in the sides 112*a*, 112*b* of the table 112. In the exemplary embodiment shown in FIGS. 1 through 5, a first of the clamps 150 is permanently fixed to the end 118*a* of the lock bar 118, with a screw for example, while the second of the clamps 160 is adjustably secured to the other end 118*b* of the lock bar 118. During use, the lock bar 118 is moved to a desired position on the table 112, the adjustable clamp 160 is moved on the lock bar 118 towards the fixed clamp 150 until the table 112 is securely clamped between the clamps 150, 160 such that the lock bar 118 is fixed on the table 112, and then the adjustable clamp 160 is locked, or fixed in place on the lock bar 118. Thereafter, a patient positioning device can be secured to the upwardly extending studs 32 of the lock bar 118.

Figure 3:
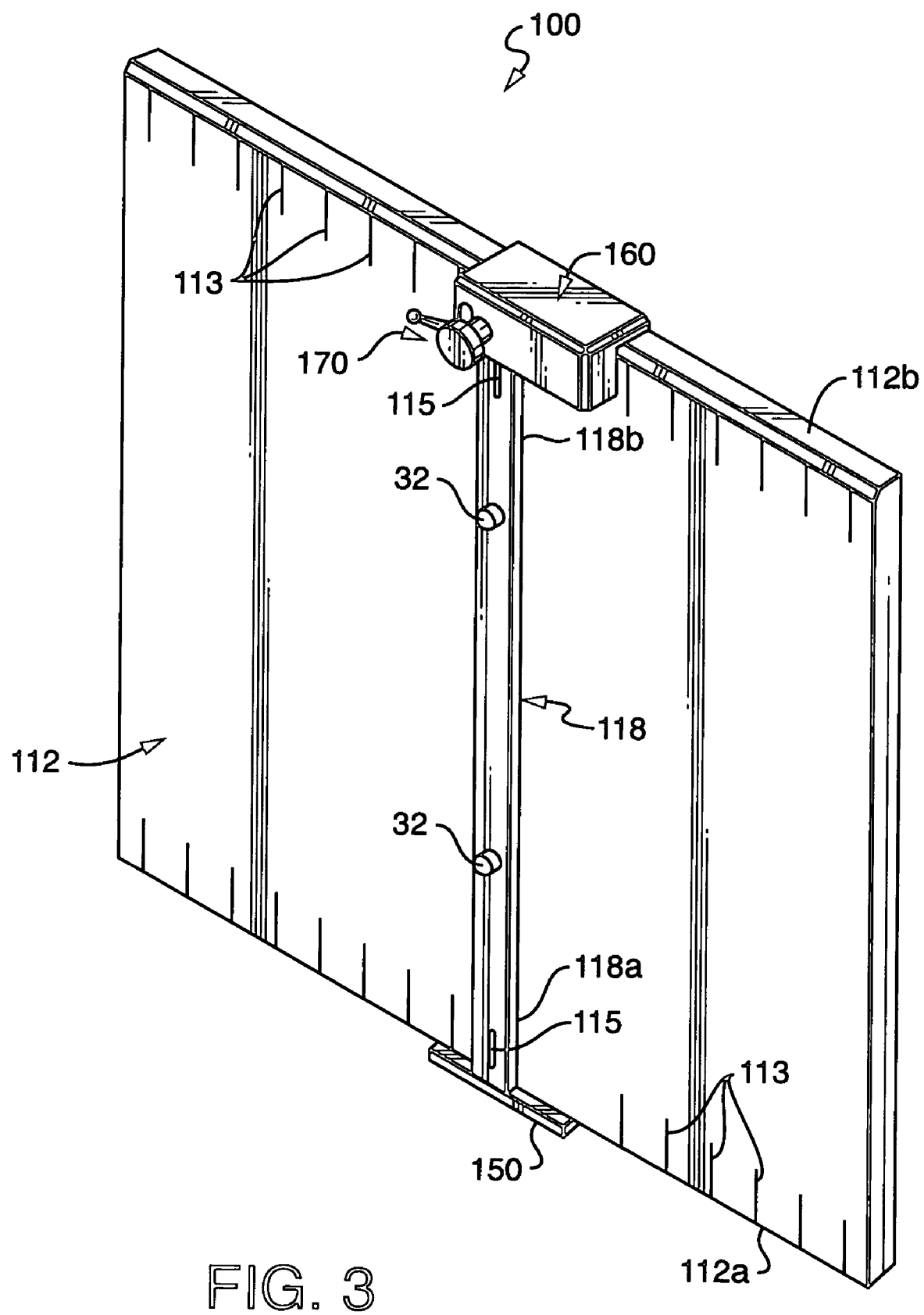
FIG. 3 is a perspective view of the lock bar and the table of FIG. 1.

As shown best in FIGS. 1 and 3, the table 112 can be provided with alignment aids for precisely positioning the lock bar 118 on the table 112. In the exemplary embodiment shown, the alignment aid comprises a graduated scale 113 or scales having positioning graduations on each sides 112*a*, 112*b* of the table 112, and an edge of the lock bar 118 will be used for alignment with the graduation scale 113. In addition, the lock bar may include a viewing slot 115 for alignment with the positioning graduations 113. The graduations 113 may extend fully across the table 112, as shown in FIG. 1 or may just be provided on the side 112*a*, 112*b* as shown in FIG. 3. The alignment aid 113, 115 can be used by an operator or technician to ensure proper and repeatable positioning of the lock bar 118 on the table 112, and ensure that the ends 118a, 118b of the lock bar 118 are evenly positioned on the table sides 112a, 112b.

In the exemplary embodiment shown, an adjustment and locking mechanism 170 adjustably secures the movable clamp 160 to the end 118b of the lock bar 118. As shown best in FIG. 4, the adjustable clamp 160 includes a cover 162 that fits over the end 118a of the lock bar 118, an end wall 164 secured to the cover 162 for engaging the side 112b of the table 112, and lips 166 secured to the end wall 164 for engaging an underside of the table 112. The cover 162 includes a groove 167 in a top surface and a hole 168 in a side surface.

Figure 5:
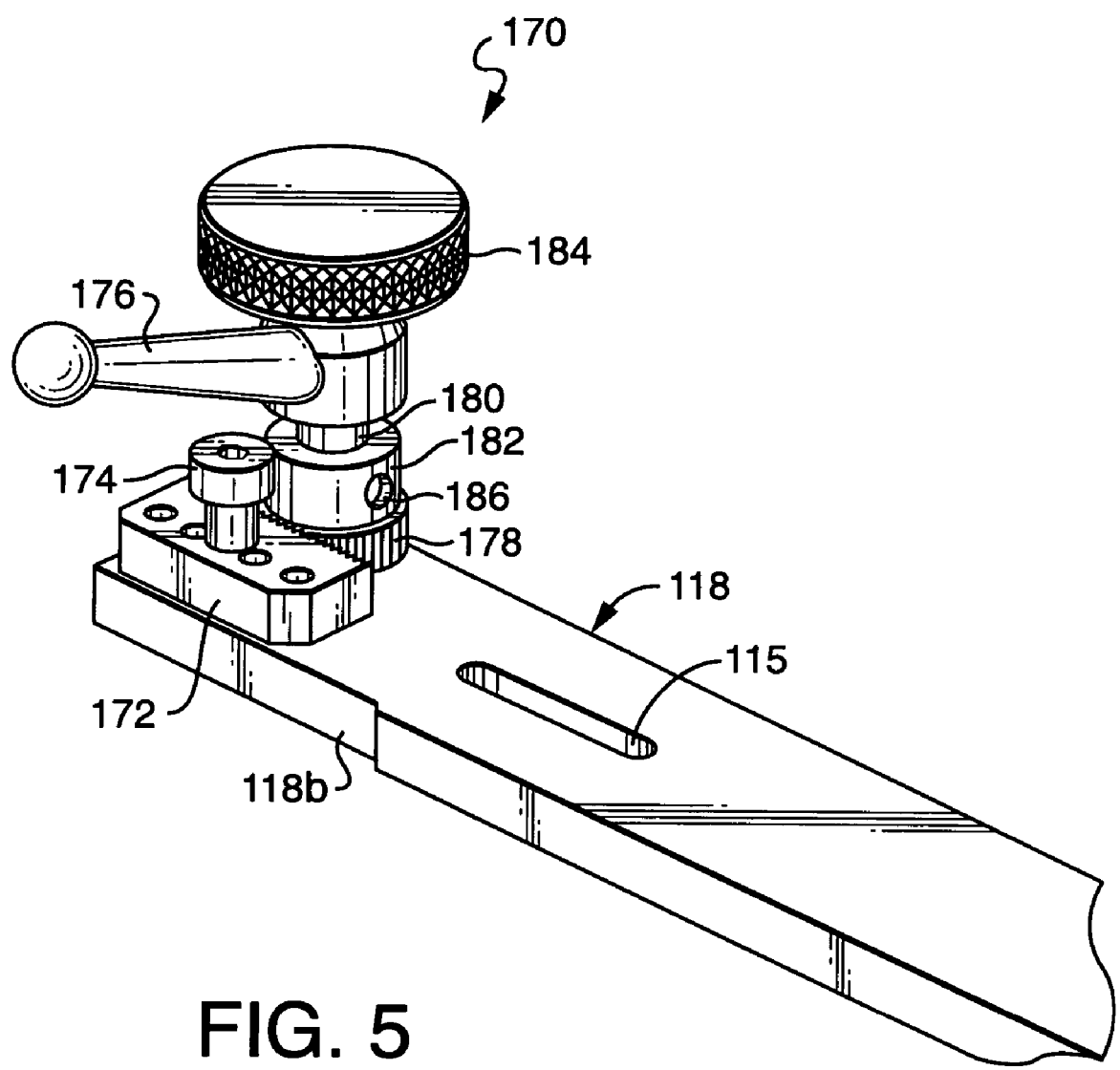
FIG. 5 is an enlarged perspective view of the adjustment and locking mechanism secured to the end of the lock bar of FIG. 1.

As shown best in FIG. 5, an exemplary embodiment of the adjustment and locking mechanism 170 includes a rack 172 secured to the end 118b of the lock bar 118 with a fastener 174, an adjustment knob 184 secured to a gear 178 through a shaft 180, and a locking knob 184 screw-threadedly received on the shaft 180. The gear 178 has a collar 182 has a bore 186 in a side thereof. Although not shown, a set screw is received through the bore 186 to secure the collar 182 and the gear 178 to the shaft 180. The gear 178 includes teeth which engage teeth of the rack 172, such that rotation of the gear 178 causes the gear to move linearly with respect to the rack 172.

Figure 4:
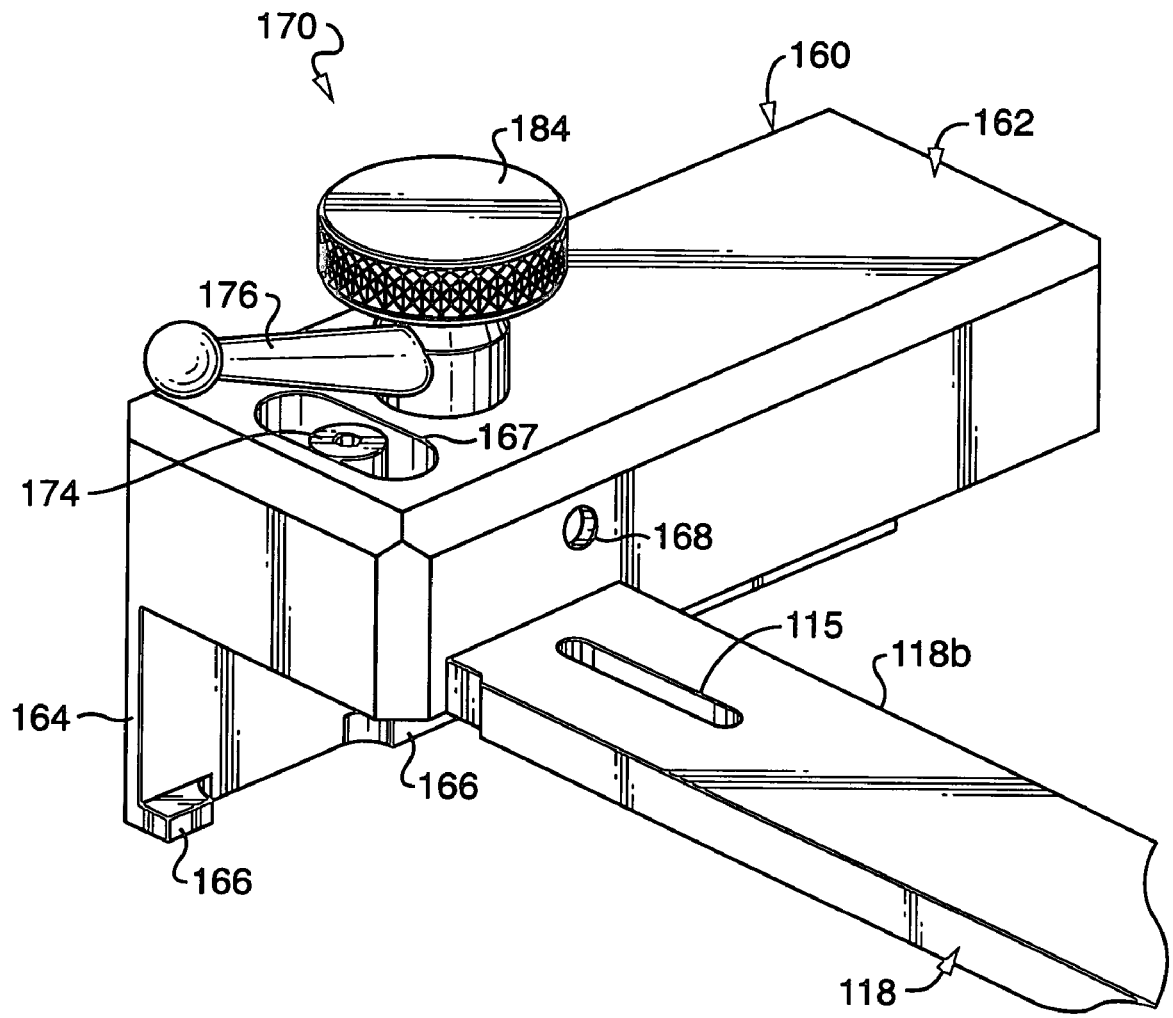
FIG. 4 is an enlarged perspective view of a movable clamp and an adjustment and locking mechanism securing the movable clamp to an end of the lock bar of FIG. 1.

Referring to FIG. 4, the fastener 174 extends through the groove 167 of the cover 162 of the adjustable clamp 160 and acts to guide movement of the adjustable clamp on the end 118b of the lock bar 118. The hole 168 in the side surface of the cover 162 allows tool access to the set screw in the bore 186 of the collar 182 of the gear 178 of the adjustment and locking mechanism 170 in order to secure the collar 182 and gear 178 to the shaft 180 through the cover 162. The shaft 180 of the adjustment and locking mechanism 170 extends through the top surface of the cover 162, and the adjusting knob 184 and the locking knob 176 are mounted on the shaft 180 outside of the cover 162.

Turning the adjustment knob 184 causes the gear 178 to rotate and move linearly with respect to the rack 172, such that the clamp 160 also moves with respect to the rack 172 and the end 118b of the lock bar 118. The rack 172 and the groove 167 of the cover 162 of the adjustable clamp 160 are both arranged such that the adjustable clamp 160 can only move in a linear direction away from or towards the fixed clamp 160. Rotation of the adjustment knob 184 in a clockwise direction, for example, moves the adjustable clamp 160 towards the fixed clamp 150 at the opposite end of the lock bar, while rotation of the adjustment knob 184 in a counter-clockwise direction moves the adjustable clamp 160 away from the fixed clamp 150.

The locking knob 176 can then be rotated (e.g., in a clockwise direction) and screwed on the shaft 180 until the locking knob connects the cover 162 to prevent rotation of the shaft 180. The locking knob 176 screwed against the cover 162 acts to fix the gear 178 in place with respect to the rack 172 and, therefore, acts to fix the adjustable clamp 160 with respect to the lock bar 118. Rotating the locking knob 176 in an opposite direction (e.g., in a counter-clockwise direction) frees the adjustable clamp 160 so that it can be moved on the lock bar 118.

It should be understood that the embodiments of the present disclosure described herein are merely exemplary and that a person skilled in the art may make variations and modifications to the embodiments described without departing from the spirit and scope of the present disclosure. All such equivalent variations and modifications are intended to be included within the scope of this disclosure as defined by the appended claims. None of the present disclosure is meant to be disclaimed.

What is claimed is:

1. A patient positioning system for radiation therapy treatment, comprising:
    an elongated table having a top surface, a length extending between opposing ends of the table, and having a width defined between opposing sides of the table, wherein the length of the table extends perpendicular to the width of the table;
    an elongated lock bar positioned on the top surface of the table and extending perpendicular to the length of the table;
    a first clamp configured to be secured at one of two opposing ends of the lock bar;
    a second clamp configured to be secured at the other of the two opposing ends of the lock bar, wherein the clamps have flat surfaces adapted to grip flat surfaces of the sides of the table so as to lock the lock bar in a fixed position between the opposing ends of the table, and wherein the clamps each include a lip for catching a bottom surface of the table, wherein the second clamp is adjustably secured on the lock bar so that the second clamp can be unsecured from the lock bar, the lock bar can be re-positioned on the table as desired between the opposing ends of the table, and the second clamp then re-secured to the lock bar to fix the lock bar securely in place on the table, and wherein the second clamp comprises a cover receivable over the end of the lock bar; and an end wall secured to the cover for engaging the flat surface of the side of the table, wherein the lip of the second clamp is secured to the end wall for catching the bottom surface of the table; and
    a patient restraint member configured to be secured to the lock bar and adapted to extend over a portion of a patient lying on the top surface of the table, in order to reproducible position the patient on the table for radiation therapy treatment.

2. A patient positioning system according to claim 1, wherein the lock bar includes a pair of upwardly extending studs adapted to be received within holes of the patient restraint member to secure the patient restraint member to the lock bar.

3. A patient positioning system according to claim 1, wherein the first clamp is permanently fixed to the end of the lock bar.

4. A patient positioning system according to claim 1, wherein the table includes alignment aids for precisely positioning the lock bar on the table.

5. A patient positioning system according to claim 4, wherein the alignment aids comprise a graduated scale having positioning graduations on each of the sides of the table.

6. A patient positioning system according to claim 5, wherein the look bar includes viewing slots for alignment with the positioning graduations.

7. A patient positioning system according to claim 1, wherein the second clamp further includes an adjustment and locking mechanism for adjustably securing the second clamp to the end of the lock bar, and the adjustment and locking mechanism comprises:
    a rack secured on the lock bar with a fastener, the fastener passing though a slot in the cover of the second clamp, wherein the slot of the cover extends parallel with the lock bar;

a rotatable gear having teeth engaging linear teeth of the rack such that rotation of the gear causes the gear to move linearly with respect to the rack, and wherein the rack is oriented on the lock bar such that linear movement of the gear is parallel with a length of the lock bar;

an adjustment knob secured to the gear through a shaft passing through an opening of the cover of the second clamp; and a locking knob received on the shaft, wherein external threads of the shaft engage internal threads of the locking knob such that rotating the locking knob until the locking knob contacts the cover of the second clamp prevents rotation of the gear and releasably fixes the gear with respect to the rack.

8. A patient positioning system for radiation therapy treatment comprising:

an elongated table having a top surface, a length extending between opposing ends of the table, and having width defined between opposing sides of the table, wherein the length of the table extends perpendicular to the width of the table;

an elongated lock bar positioned on the top surface of the table and extending perpendicular to the length of the table;

a first damn configured to be secured at one of two opposing ends of the lock bar;

a second clamp configured to be secured at the other of the two opposing ends of the lock bar, wherein the damns have flat surfaces adapted to grip flat surfaces of the sides of the table so as to lock the lock bar in a fixed position between the opposing ends of the table, and wherein the clamps each include a lip for catching a bottom surface of the table, wherein the second damn is adjustably secured on the lock bar so that the second damn can be unsecured from the lock bar, the lock bar can be re-positioned on the table as desired between the opposing ends of the table, and the second clamp then re-secured to the lock bar to fix the lock bar securely in place on the table; and a patient restraint member configured to be secured to the lock bar and adapted to extend over a portion of a patient lying on the top surface of the table, in order to reproducible position the patient on the table for radiation therapy treatment, wherein the second clamp further includes an adjustment mechanism comprising:

a rack secured on the lock bar;

a rotatable gear having teeth engaging liner teeth of the rack such that rotation of the sear causes the gear to move linearly with respect to the rack, and wherein the rack is oriented on the lock bar such that linear movement of the gear is parallel with a length of the lock bar;

an adjustment knob secured to the gear through a shaft secured to the second clamp.

9. A patient positioning system according to claim 8, wherein the mechanism further includes a locking knob received on the shaft, wherein external threads of the shaft engage internal threads of the locking knob such that rotating the locking knob until the locking knob contacts a fixed portion of the second clamp prevents rotation of the gear and releasably fixes the gear with respect to the rack.

10. A patient positioning device for radiation therapy treatment, comprising:

an elongated table extending along a length of the table between opposing ends of the table, and having a width defined between opposing sides of the table;

an elongated lock bar positioned on a top surface of the table and extending perpendicular to the length of the table;

a first clamp secured at one of two opposing ends of the lock bar;

a second clamp secured at the other of the two opposing ends of the lock bar, wherein the clamps have flat surfaces adapted to grip flat surfaces of the sides of the table so as to lock the lock bar in a fixed position between the opposing ends of the table, and wherein the clamps each include a lip for catching a bottom surface of the table, wherein the second clamp includes an adjustment mechanism including, a rack secured on the lock bar, a rotatable gear having teeth engaging linear teeth of the rack such that rotation of the gear causes the gear to move linearly with respect to the rack, and wherein the rack is oriented on the lock bar such that linear movement of the gear is parallel with a length of the lock bar, and an adjustment knob secured to the gear through a shaft.

11. A patient positioning device according to claim 10, wherein the lock bar includes a pair of upwardly extending studs adapted to be received within holes of the patient restraint member to secure the patient restraint member to the lock bar.

12. A patient positioning device according to claim 10, wherein the first clamp is permanently fixed to the end of the lock bar.

13. A patient positioning device according to claim 10, wherein the table includes alignment aids for precisely positioning the lock bar on the table.

14. A patient positioning device according to claim 13, wherein the alignment aids comprise a graduated scale having positioning graduations on each of the sides of the table.

15. A patient positioning device according to claim 14, wherein the lock bar includes viewing slots far alignment with the positioning graduations.

16. A patient positioning device according to claim 10, wherein the mechanism further includes a locking knob secured to the shaft, wherein external threads of the shaft engage internal threads of the locking knob such that rotating the locking knob until the locking knob contacts a fixed portion of the second clamp prevents rotation of the gear and releasably fixes the gear with respect to the rack.

17. A patient positioning system for radiation therapy treatment, comprising:

an elongated table having a length extending between opposing ends of the table, and having a width defined between opposing sides of the table;

an elongated lock bar positioned on a top surface of the table and extending perpendicular to the length of the table;

first and second clamps secured to opposing ends of the lock bar, wherein the clamps have flat surfaces adapted to grip flat surfaces of the sides of the table so as to lock the lock bar in a fixed position between the opposing ends of the table, and wherein the second clamp includes an adjustment mechanism including a rack secured on one of the lock bar and the second clamp, and a rotatable gear secured to the other of the lock bar and the second clamp, wherein the gear has teeth engaging linear teeth of the rack such that rotation of the gear causes the gear to move linearly with respect to the rack, and wherein the rack is oriented on the lock bar such that linear movement of the gear is parallel with a length of the lock bar; and a patient restraint member secured to the lock bar and adapted to extend over a portion of a patient lying on the top surface of the table, in order to reproducible position the patient on the table for radiation therapy treatment.

18. A patient positioning system according to claim 17, wherein the table includes alignment aids for precisely positioning the lock bar on the table, arid the alignment aids comprise a graduated scale having positioning graduations on each of the sides of the table.

19. A patient positioning system according to claim 18, wherein the lock bar includes viewing slots for alignment with the positioning graduations.

* * * * *